United States Patent

Timmerman et al.

Patent Number: 5,420,143
Date of Patent: May 30, 1995

[54] PIPERIDINE DERIVATIVES FOR TREATING ALLERGY

[75] Inventors: Henk Timmerman, Voorschoten; Zhang Mingiang, Amstelveen, both of Netherlands

[73] Assignee: Kowa Co., Ltd., Nagoya, Japan

[21] Appl. No.: 199,842

[22] Filed: Feb. 22, 1994

[30] Foreign Application Priority Data

Mar. 5, 1993 [JP] Japan ................. 5-045156

[51] Int. Cl.⁶ .................. C07D 405/12; A61K 31/445
[52] U.S. Cl. ..................................... 514/320; 546/196
[58] Field of Search .................... 514/320; 546/196

[56] References Cited

U.S. PATENT DOCUMENTS

| | | | |
|---|---|---|---|
| 4,950,674 | 8/1990 | Yanni et al. | 514/317 |
| 5,250,681 | 10/1993 | Shoji | 540/577 |
| 5,286,735 | 2/1994 | Bonnaud | 514/321 |

FOREIGN PATENT DOCUMENTS 0485984  5/1992  European Pat. Off.

OTHER PUBLICATIONS

Journal of Medicinal Chemistry, vol. 32, No. 1, Jan. 1989, David A. Walsh, et al., "Synthesis and Antiallergy Activity of 4-(Diarylhydroxymethyl)-1-[-3-(Aryloxy)Proptyl]Piperidines and Structurally Related Compounds", pp. 105–118.

*Primary Examiner*—Celia Chang
*Attorney, Agent, or Firm*—Oblon, Spivak, McClelland, Maier & Neustadt

[57] ABSTRACT

A piperadine derivative of formula (1):

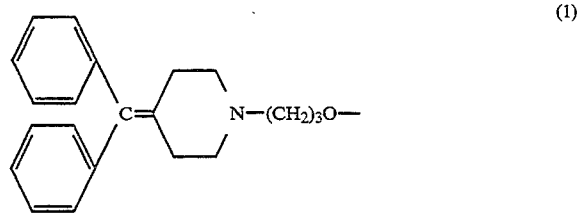

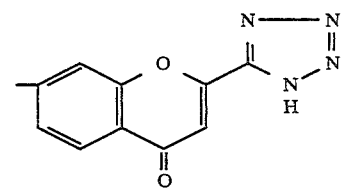

a salt thereof and a drug containing the derivative as an effective component.

This compound has excellent antihistamine activity and antileukotriene activity, which are well balanced, and thus they are useful for the prevention and treatment of asthma or other allergic diseases such as allergic rhinitis, allergic dermatosis and urticaria.

6 Claims, No Drawings

PIPERIDINE DERIVATIVES FOR TREATING ALLERGY

BACKGROUND OF THE INVENTION

1. Field of the Invention

The present invention relates to a piperidine derivative or a salt thereof, which has excellent antihistamine activity and antileukotriene activity, and is useful as a drug for the prevention and treatment of various allergic diseases.

2. Description of the Background

Histamine produces various complex biological actions via interaction with specific receptors in the membranes of cell surfaces. Action of histamine on $H_1$-receptors stimulates many smooth muscles to contract such as those in the bronchi. Contraction of the bronchi leads to restriction of the air passage into and out of the lungs as in asthma. Histamine also increases the permeability of the capillary walls so that more of the constituents of the plasma can escape into the tissue spaces, leading to an increase in the flow of lymph and its protein content, and formation of edema. Histamine $H_1$-receptor antagonists have been proven to be successful for the treatment of many allergic diseases, e.g., allergic rhinitis, dermatosis, urticaria, etc. However for the treatment of some severe allergic diseases such as asthma, histamine $H_1$-receptor antagonists have been found to be less effective.

Leukotrienes are a group of arachidonic acid metabolites which are collectively long-known 'slow-reacting substance of anaphylaxis' (SRS-A). The biological action of leukotrienes include bronchoconstriction, mucus hypersecretion and pulmonary edema which all contribute to airway obstruction characteristic of asthma. Leukotrienes also possess chemotactic properties that attract leukocyte to sites of cellular injury and thus contribute to inflammation. In contrast to histamine, leukotrienes induce prolonged bronchoconstriction. Clinical trials of the compounds known to have capability to block leuokotriene $D_4$ ($LTD_4$) action on its receptors have shown that these compounds are effective for the treatment of asthma (Manning, P. J. et al: N. Engl. J. Med. 1990, 323, 1736–1739 and Taylor, I. K. et al: Lancer 1991, 337, 690–694).

Accordingly, compounds with antagonistic activity on both histamine $H_1$-receptors and leukotriene $LTD_4$-receptors are potentially useful therapeutics for the prevention and treatment of allergic diseases in general and asthma in particular.

Many piperidine derivatives have been reported to exhibit both antihistamine activity and antileukotriene activity (Foxwell, M. H. et al: J. Allergy Clin. Immunol. 1988, 81, 250; European patent publication No. 0399414A1; Japanese patent publication (kokai) No. 271458/1991; and Japanese patent publication (kokai) No. 182467/1992).

These conventional piperidine derivatives, however, exhibit only insufficient pharmacological activities. Accordingly, compounds having potent antihistamine and antileukotriene activities with extensively reduced adverse side-effects such as a central nervous system inhibitory action have still been desired.

Under the above circumstances, the present inventors have carried out earnest studies for providing a compound which possesses excellent antihistamine activity and antileukotriene activity, is very safe and is useful for the prevention and treatment of asthma, allergic rhinitis, allergic dermatosis, urticaria, etc.

SUMMARY OF THE INVENTION

An object of the present invention is to provide a piperidine derivative represented by the formula (1):

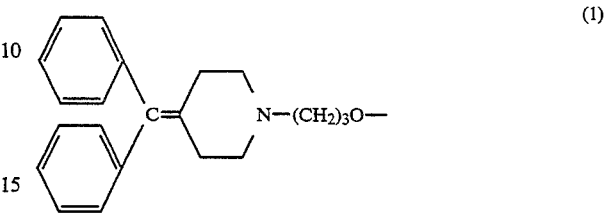

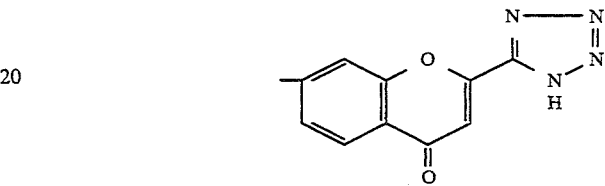

and a salt thereof.

Another object of the present invention is to provide an antihistamine drug, antileukotriene drug and an antiallergy drug which comprise a piperidine derivative of formula (1) as an effective component.

DETAILED DESCRIPTION OF THE INVENTION AND PREFERRED EMBODIMENTS

The present inventors have synthesized many piperidine derivatives, have investigated their pharmacological activities, and have found that the compounds represented by the formula (1) have excellent antihistamine activity and antileukotriene activity, are very safe and are useful for the prevention and treatment of allergic diseases such as asthma, with extensively reduced side-effects such as a central nervous system inhibitory action.

No particular limitation is imposed on the salts of the compounds represented by formula (1) as long as they are pharmacologically acceptable. Examples of such salts include acid adducts of mineral acids, such as hydrochlorides, hydrobromides, hydriodides, sulfates and phosphates; acid adducts of organic acids, such as benzoates, methane sulfonates, ethane sulfonates, benzene sulfonates, p-toluene sulfonates, oxalates, maleates, fumarates, tartarates and citrates; and metal salts such as sodium salts, potassium salts, calcium salts, magnesium salts, manganese salts, iron salts and aluminum salts.

The present compounds (1) and their salts are prepared, for example, by the following reaction scheme:

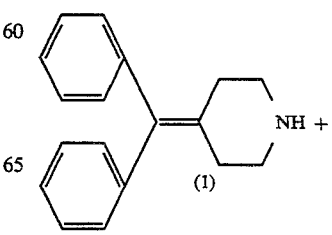

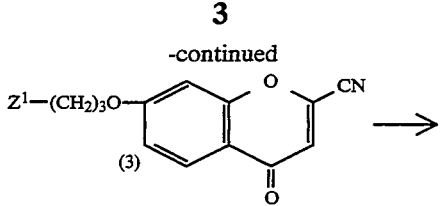
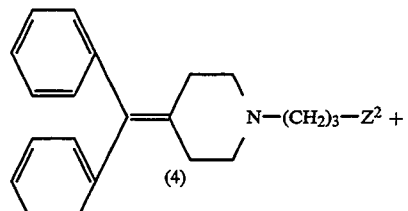
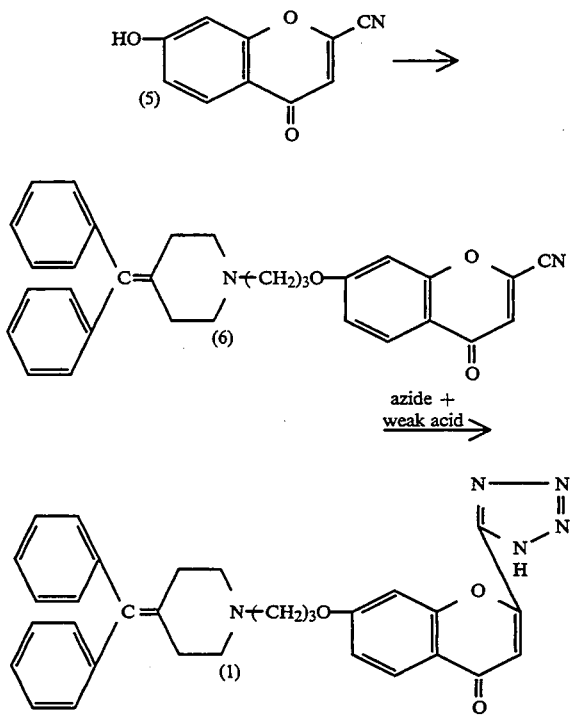

wherein $Z^1$ is an atom or a group which can be eliminated, such as a halogen atom, a methane sulfonyloxy group, a paratoluene sulfonyloxy group, and $Z^2$ is a halogen atom.

In other words, the present compounds (1) can be obtained by reacting compound (2) with compound (3), or reacting compound (4) with compound (5) to give an intermediate (6), then reacting an azide and a weak acid with the intermediate (6).

The compound (3) which is useful in the process of preparing the present invention can be prepared, for example, by reacting ω-chlorobromoalkane with a hydroxy substituted 4-oxo-4H-benzopyran in the presence of a base.

The reactions between compound (2) and compound (3) or between compound (4) and compound (5) are preferably proceed in the presence of a base. Examples of suitable bases include tertiary amines such as triethylamine, tributylamine, pyridine, picoline, lutidine and collidine; metal alkoxides such as sodium methoxide and sodium ethoxide; inorganic bases such as potassium carbonate, sodium carbonate and sodium hydrogencarbonate. Examples of suitable reaction solvents include aromatic hydrocarbons such as benzene and toluene; ethers such as tetrahydrofuran and dioxane; non-polar organic solvents such as acetone and acetonitrile; alcohols such as methanol, ethanol, isopropanol and n-butanol; polar organic solvents such as dimethyl sulfoxide and N,N-dimethylformamide. The reaction preferably proceeds at room temperature or with heating.

Examples of azides which are useful in the tetrazolyl reaction of compound (6) include sodium azide, lithium azide and potassium azide. Examples of weak acids which are useful in the present invention include pyridinium chloride, ammonium chloride and dimethylaniline hydrochloride. The reaction preferably proceeds under anhydrous condition in the presence of a polar solvent such as dimethylformamide or N-methylpyrrolidone with heating.

After completion of the reaction, a suitable treatment of the obtained compound according to a conventional manner will provide the target compound of the present invention, which may further be purified by an ordinary purification process such as recrystallization, column chromatography, etc., as desired. If necessary, the compound may be converted into the aforementioned salts by a method known per se.

The thus obtained compounds (1) and their salts exhibit excellent antihistamine activity and excellent antileukotriene $D_4$ activity as shown in the Examples below, and therefore, they are very useful in the prevention and treatment of various allergic diseases of the human and animals. As to the manner of administration of the present compounds as a drug for preventing or treating the allergic diseases, mention may be given to oral administrations by way of tablets, capsules, granule, powder and syrup; and non-oral administrations such as intravenous injection, intramuscular injection, suppositories, inhalation, percutaneous absorption, eye drops and nasal drops. In order to prepare a medicine in the above mentioned various physical forms, conventional additional components known per se may further be employed in a suitable combination, which include excipients, binders, disintegulators, surfactants, lubricants, dispersing agents, buffering agents, preservatives, flavors, perfumes, coating agents, etc.

The dosage of the compound of the present invention for the prevention and treatment of allergic diseases varies depending on the age, weight, symptom, manner of administration, frequency of the administration, etc. In general, it is preferred to administer the compound of the present invention to an adult in an amount of from about 1 to 1000 mg/day once or as divided in several times, orally or non-orally.

EXAMPLES

The present invention will now be explained by way of examples, which however, should not be construed as limiting the invention thereto.

EXAMPLE 1

7-[3-(4-Diphenylmethylenepiperidin-1-yl)propyloxy]-2-(5-tetrazolyl)-4-oxo-4H-benzopyran: Compound (1)

(1) A mixture of 2.43 g (13 mmol) of 2-cyano-7-hydroxy-4-oxo-4H-1-benzopyran, 2.04 g (13 mmol) of 3-chlorobromopropane and 1.80 g (13 mmol) of potassium carbonate was refluxed in 250 ml dry acetone overnight with heating. After evaporating to dryness, the residue was extracted with chloroform (3×100 ml), and dried with sodium sulfate. The chloroform solution was evaporated to one-third of the original volume to which was added n-hexane. The white precipitate was collected by filtration, washed with n-hexane and dried in vacuum to obtain 2-cyano-7-(3-chloropropyloxy)-4-oxo-4H-1-benzopyran (yield 51%).

mp: 124°–125° C.

$^1$H-NMR(CDCl$_3$) δ (ppm): 2.31 (m, 2H, CH$_2$CH$_2$CH$_2$) 3.77 (t, 2H, J=6.1 Hz, ClCH$_2$) 4.24 (t, 2H, J=5.9 Hz, CH$_2$O) 6.77 (s, 1H, C$_3$—H) , 6.90 (d, 1H, J=2.3 Hz, C$_8$—H) , 7.04 (m, 1H, C$_6$—H) , 8.09 (d, 1H, J=8.9 Hz, C$_5$—H)

(2) A mixture of 0.4 g (1.5 mmol) 2-cyano-7-(3-chloropropyloxy)-4-oxo-4H-1-benzopyran, 0.38 g (1.5 mmol) 4-diphenylmethylenepiperidine, 0.225 g (1.5 mmol) sodium iodide and 0.21 g (1.5 mmol) potassium carbonate in 200 ml dry acetone was refluxed for 48 hours. After removing the solvent, the solid residue was extracted with chloroform. The chloroform solution was evaporated to dryness and the residue was put on a silica gel column and eluated with a mixture of diethylether/ethyl acetate(5:1). Removing the solvents of the collected fractions (Rf=0.39) afforded the compound (6), 2-cyano-7-[3-(4-diphenylmethylenepiperidin-1-yl)propyloxy]-4-oxo-4H-benzopyran as a thick colorless oil (yield: 79%).

$^1$H-NMR(CDCl$_3$) δ (ppm): 2.02(m, 2H, CH$_2$CH$_2$CH$_2$) 2.36–2.58 (m, 10H, piperidine H & CH$_2$CH$_2$CH$_2$N) 4.10(t, 2H, J=6.1 Hz, CH$_2$O) 6.76(s, 1H, chromone C$_3$—H) 6.89(d, 1H, J=2.3 Hz, chromone C$_8$—H) 7.01(m, 1H, chromone C$_6$—H) 7.10–7.30 (m, 10H, phenyl H ) 8.06(d, 1H, J=9.0 Hz, chromone C$_5$—H)

(3) A mixture of 0.57 g (1.2 mmol) of compound (6), 0.47 g (7.2 mmol) sodium azide and 0.39 g (7.2 mmol) ammonium chloride in 50 ml dry N,N-dimethylformamide was stirred at 120° C. under nitrogen overnight. After evaporating to dryness, to the residue was added water and extracted with chloroform. The combined chloroform solution was dried with sodium sulfate and evaporated to dryness. The collected fractions (Rf=0.20) was purified on a silica gel column using a mixture of ethyl acetate/methanol (2:1) as an eluate to obtain the compound (1) as yellow crystals (yield: 77%).

mp: 224°–225° C.

$^1$H-NMR (DMSO-d$_6$) δ (ppm): 1.96 (m, 2H, CH$_2$CH$_2$CH$_2$) 2.29–2.52 (m, 10H, piperidine H & CH$_2$CH$_2$CH$_2$N) 4.21(t, 2H, J=6.0 Hz, CH$_2$O) 6.80(s, 1H, chromone C$_3$—H) 7.02–7.35(m, 12H, phenyl H & chromone C$_{6,8}$ —H)

TEST EXAMPLE 1

Antihistamine activity and antileukotriene activity:

A piece of the ileum (about 1.5 cm in length) isolated from guinea pigs was trimmed, tied at both ends and mounted in a 20 ml organ bath containing Krebs buffer (37° C., constantly bubbled with 95% O$_2$—5% CO$_2$). The Krebs buffer had the following composition in mmol/l: NaCl 117.5; KCl 5.6; CaCl$_2$ 2.5; NaH$_2$PO$_4$ 1.28; MgSO$_4$ 1.18; NaHCO$_3$ 25; and glucose 5.5. The first three constant constractions induced by histamine ($1 \times 10^{-5}$ M) or leukotriene D$_4$($1 \times 10^{-8}$ M) were used as the reference for the calculation of the inhibitory ratio. After repeated washings until contraction movement recurred, ileal strip was incubated with the test compound for 30 minutes. The contraction test was then conducted again using histamine or leukotriene D$_4$.

The inhibitory ratio (%) of the test compound on the ileum was calculated according to the following equation:

$$\text{Inhibition ratio (\%)} = 1 - \left[ \frac{\text{Contraction induced by histamine or leukotriene } D_4}{\text{in the presence of test compound } (10^{-7} M)} \middle/ \frac{}{\text{Contraction induced by histamine or leukotriene } D_4} \right] \times 100$$
$$\text{in the absence of test compound}$$

As shown in Table 1 below, the compound of the present invention exhibited potent antihistamine activity and antileukotriene activity compared to terfenadine and FPL-55712, both of which are known compounds.

TABLE 1

| Test compound | Inhibition vs histamine-induced contraction (%) Average ± S.D. | Inhibition vs leukotriene D$_4$ induced contraction (%) Average ± S.D. |
|---|---|---|
| Compound (1) | 52 ± 7 | 15 ± 1 |
| Terfenadine | 5 ± 1 | 0 |
| FPL-55712 | 0 | 11 ± 4 |

TEST EXAMPLE 2

Binding assay on Leukotriene D$_4$ receptors:

a) Preparation of guinea-pig lung membrane protein:

Guinea-pig lungs, previously perfused in situ with Krebs buffer (pH 7.4), were chopped and homogenized in Tris-HCl/sucrose buffer (pH 7.4, 10 ml/g wet weight) and centrifuged at 900 g for 10 min. The pellet was resuspended in 5 ml/g weight Tris-HCl/sucrose buffer, homogenized and centrifuged at 900×g for another 10 minutes. The combined supernatant was then centrifuged at 32,000×g for 20 minutes. The pellet was resuspended in 1 ml Tris-HCl/sucrose buffer/mg weight and centrifuged at 32,000 g for another 20 minutes. The pellet was collected and resuspended in a Tris-HCl/piperazine -N,N'-bis(2-ethanesulfonic)acid buffer (10 mM/10 mM, pH 7.5) to a final concentration of about 1.5 mg protein/ml and stored at −80° C. until use.

b) Binding assay with receptors:

A mixture of total volume of 0.3 ml containing 0.2 nM [$^3$H]-leukotriene D$_4$, guinea-pig lung membrane proteins (±170 micrograms/ml) and the test compound in a 10 mM piperazine-N,N'-bis(2-ethanesulfonic)acid buffer (pH 7.5) was incubated at 22° C. for 30 minutes. The piperazine-N,N'-bis(2-ethanesulfonic)acid buffer contains 10 mM CaCl$_2$, 10 mM MgCl$_2$, 50 mM NaCl, 2 mM cysteine and 2 mM glycine. the reaction was terminated by the addition of 5 ml ice-cold Tris-HCl/NaCl buffer (10 mM/100 mM, pH 7.5). The mixture was immediately filtered under vacuum (Whatman GF/C filters) and the filter was washed once with 20 ml ice-cold buffer. The retained radioactivity was determined by a liquid scintillation counter.

In the saturation test, 2 micro mols of leukotriene D$_4$ was used to define the non-specific binding. A single, saturable binding site with B$_{max}$=988 fmol/mg protein was found from the saturation test. The Kd of [$^3$H]-leukotriene D$_4$ was found to be 2.16×10$^{-10}$ M and no cooperativity was determined when the data were analyzed by Hill plots (slope=0.99).

It was confirmed that the binding affinity on leukotriene $D_4$ receptors (Kd) of the compound (1) was $2.32\times10^{-6}$ M, and the antileukotriene activity of the compound of the present invention was antagonistic.

As shown above, the compound (1) of the present invention has excellent antihistamine activity and antileukotriene activity, which are well balanced, and thus, they are useful for the prevention and treatment of asthma or other allergic diseases such as allergic rhinitis, dermatosis and urticaria.

We claim:

1. A piperidine derivative of formula (1):

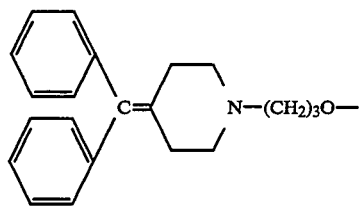

(1)

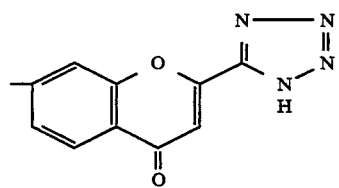

or a salt thereof.

2. A pharmaceutical composition for the treatment of allergic diseases, which comprises an anti-allergically effective amount of the piperidine derivative as defined in claim 1 or a salt thereof and a pharmaceutically acceptable excipient.

3. An antihistamine pharmaceutical composition which comprises an antihistaminically effective amount of the piperidine derivative as defined in claim 1 or a salt thereof and a pharmaceutically acceptable excipient.

4. An antileukotriene pharmaceutical composition which comprises an antileukotrienically effective amount of the piperidine derivative as defined in claim 1 or a salt thereof and a pharmaceutically acceptable excipient.

5. A method for treating allergic diseases, comprising administering to a subject in need of such treatment an anti-allergically effective amount of the piperidine derivative as defined in claim 1 or a salt thereof.

6. A method for treating asthma, allergic rhinitis, allergic dermatosis or urticaria, comprising administering to a subject in need of such treatment an amount effective for such treatment of the piperidine derivative as defined in claim 1 or a salt thereof.

* * * * *